United States Patent
Liang et al.

[11] Patent Number: 5,882,548
[45] Date of Patent: Mar. 16, 1999

[54] LUMINESCENT ORGANIC-INORGANIC PEROVSKITES WITH A DIVALENT RARE EARTH METAL HALIDE FRAMEWORK

[75] Inventors: Kangning Liang, Mohegan Lake; David Brian Mitzi, Chappaqua, both of N.Y.

[73] Assignee: International Business Machines Corporation, Armonk, N.Y.

[21] Appl. No.: 852,894

[22] Filed: May 8, 1997

[51] Int. Cl.$^6$ ............... C09K 11/06; C07F 5/00; C07C 291/00
[52] U.S. Cl. ............ 252/301.16; 534/15; 564/118
[58] Field of Search .............. 252/381.16; 534/15; 564/118

[56] References Cited

U.S. PATENT DOCUMENTS 3,079,402  2/1963  Voigt ........................ 534/15

*Primary Examiner*—Melissa Koslow
*Attorney, Agent, or Firm*—Stephens S. Strunck

[57] ABSTRACT

There is disclosed herein novel organic-inorganic layered perovskites of the general formula $A_2MX_4$ where A is an organic ammonium cation, M is a divalent rare earth metal and X is a halogen. These compounds can be made by a low temperature (about 100°–160° C.) solid state reaction between the organic ammonium salt with the appropriate hydrogen halide and $MX_2$ where M is a divalent rare earth metal and X is a halogen). A specific example is $(C_4H_9NH_3)_2EuI_4$ which has been made through a reaction at about 140°–160 C. between $C_4H_9NH_2$, HI and $EuI_2$. This new compound produces intense blue photoluminescence at room temperature, with a peak wavelength of 460 nm and a fairly narrow peak width (FWHM=24 nm). In addition to the simple aliphatic ammonium cations of the form $C_nH_{2n+1}NH_3^+$, e.g., propylammonium $(C_3H_7NH_3)$ and butylammonium $(C_4H_9NH_3)$, a wide range of organic cations including those based on aliphatic amines, simple aromatic amines and more complex organic cations will substitute into the "A" sites of the current family of novel organic-inorganic perovskites. There is also disclosed a novel perovskite of the general formula $AMX_3$, $CH_3NH_3EuI_3$, having a photoluminescence peak at 448 nm. Both families of compounds are expected to be useful in devices such as organic/inorganic light emitting diodes.

6 Claims, 6 Drawing Sheets

LUMINESCENT ORGANIC-INORGANIC PEROVSKITES WITH A DIVALENT RARE EARTH METAL HALIDE FRAMEWORK

GOVERNMENT RIGHTS

This invention was made with Government support under Contract Number DAAL01-96-C-0095 awarded by ARPA. The Government has certain rights in this invention.

BACKGROUND OF THE INVENTION

FIELD OF THE INVENTION

Generally, this invention relates to organic-inorganic perovskites of the types $A_2MX_4$ and $AMX_3$ where A=an organic cation, X=a halogen and "M"=a divalent metal cation. More particularly, this invention relates to organic-inorganic perovskites of the $A_2MX_4$ and $AMX_3$ types having a divalent rare earth metal atom in the M site.

DESCRIPTION OF PRIOR ART

There are currently two classes of the organic-inorganic perovskites, $A_2MX_4$, where A=organic cation and X=halogen, based on the divalent metal "M" in the inorganic component of the structure. Compounds with transition metal atoms occupying the "M" site have been studied for a number of years, primarily for the interesting magnetic properties and structural transitions that result from the lower-dimensional extended inorganic anions and the versatile organic cation layer which separates them. More recently, systems with the group 14 elements (Ge, Sn, and Pb) in the metal site have generated considerable interest for their conducting and luminescent properties. A semiconductor-metal transition was found in the multilayer perovskites, $(C_4H_9NH_3)_2(CH_3NH_3)_{n-1}Sn_nI_{3n+1}$, as a function of increasing thickness of the perovskite sheets. Intense room temperature photoluminescence has also been observed in the Sn(II) and Pb(II) systems, at wavelengths ranging from the ultraviolet through the red spectral region. The ability to tune the wavelength through the choice of metal atom, halogen, or the thickness of the perovskite sheets has also been achieved.

Recently, an electroluminescent device has been demonstrated, using phenethylammonium lead(II) iodide, $(C_6H_5C_2H_4NH_3)_2PbI_4$, as an emitter material, producing highly intense green luminescence of more than 10,000 cd m$^{-2}$ (at liquid nitrogen temperature), with a current density of 2 A cm$^{-2}$. The combination of the potentially useful optical and transport properties and the range of materials processing options, which include growing sizable single crystals from near-ambient temperature solutions, and spin-coating or thermal evaporation of thin films, suggests that these materials might be attractive candidates for incorporation into light-emitting devices. Before this can happen, however, it is necessary to improve the room temperature luminescent efficiency of this class of materials.

SUMMARY OF THE INVENTION

There is disclosed herein novel organic-inorganic layered perovskites of the general formula $A_2MX_4$ where A is an organic ammonium cation, M is a divalent rare earth metal and X is a halogen. These compounds can be made by a low temperature (about 100°–160° C.) solid state reaction between the organic ammonium salt with the appropriate hydrogen halide and $MX_2$ where M is a divalent rare earth metal and X is a halogen. A specific example is $(C_4H_9NH_3)_2EuI_4$ which has been made through a reaction, at about 140°–160° C., between $C_4H_9NH_2 \cdot HI$ and $EuI_2$. This new compound produces intense blue photoluminescence at room temperature, with a peak wavelength of 460 nm and a fairly narrow peak width (FWHM=24 nm), a wavelength which is red-shifted approximately 18 nm relative to that for $EuI_2$. In contrast to $(C_4H_9NH_3)_2MI_4$ (M=Sn, Pb), for which mobile Wannier excitons radiatively decay to produce luminescence, the strong emission in $(C_4H_9NH_3)_2EuI_4$ is believed to arise from a more localized excitation between the Eu$^{2+}$ ground state, 4f$^7$, and the 4f$^6$5d$^1$ configurations.

It is expected that in addition to the simple aliphatic ammonium cations of the form $C_nH_{2n+1}NH_3^+$, e.g., propylammonium ($C_3H_7NH_3$) and butylammonium ($C_4H_9NH_3$), a wide range of organic cations, including those based on aliphatic amines, simple aromatic amines and more complex organic cations, will substitute into the "A" sites of the current family of novel organic-inorganic perovskites. There is also disclosed a novel perovskite of the general formula $AMX_3$, $CH_3NH_3EuI_3$, having a photoluminescence peak at 448 nm. Both families of compounds are expected to be useful in devices such as organic/inorganic light emitting diodes.

BRIEF DESCRIPTION OF THE DRAWINGS

The above and other advantages of this invention will become more apparent from the following description taken in conjunction with the accompanying drawings, in which.

DETAILED DESCRIPTION OF THE INVENTION

Figure 1:
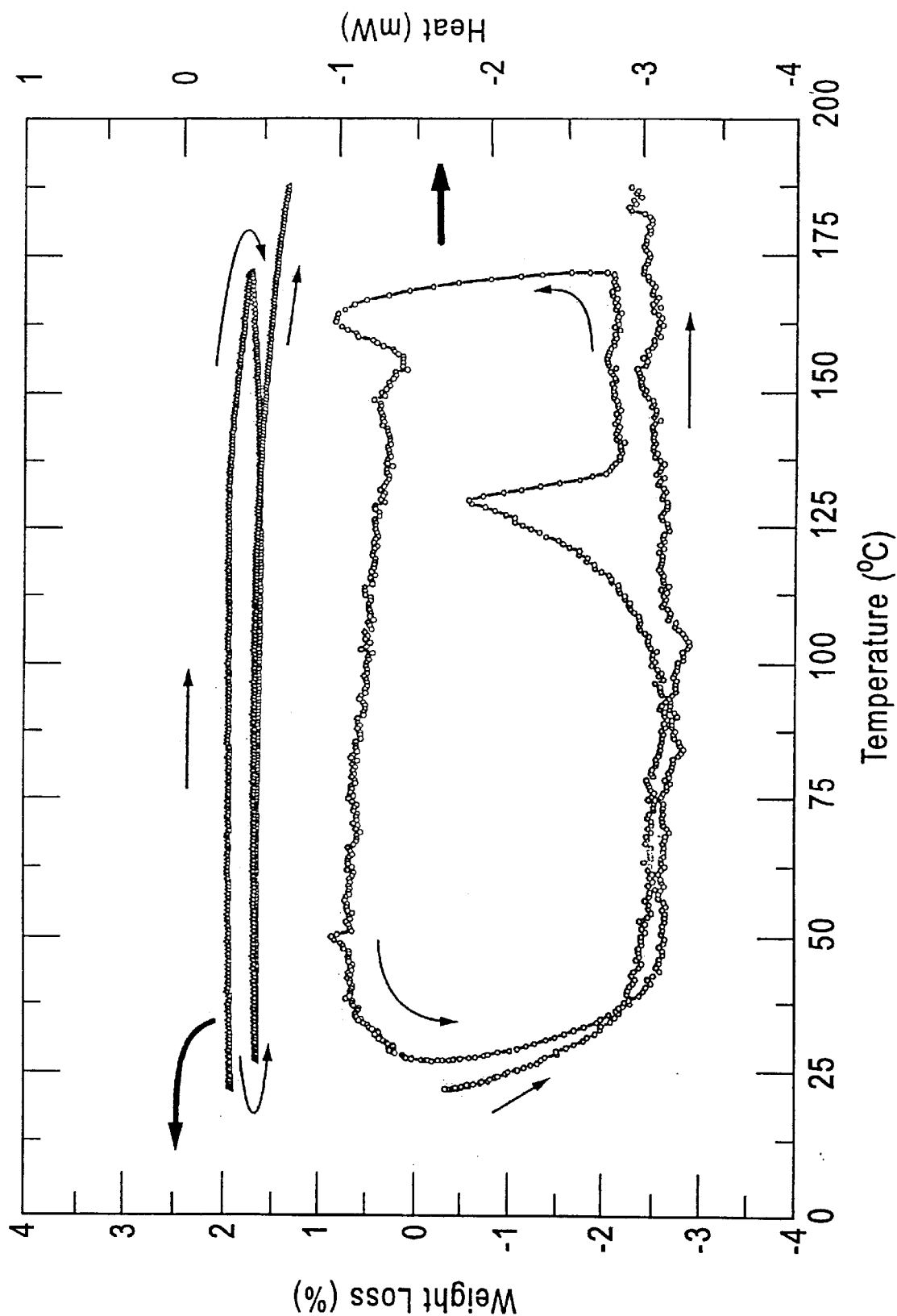
FIG. 1 shows the simultaneous thermogravimetric analysis (TGA) and differential thermal analysis (DTA) scans for a previously unreacted stoichiometric (2:1) mixture of $C_4H_9NH_2 \cdot HI$ and $EuI_2$ wherein the temperature was ramped at 2° C./min from 20° C. to 175° C., back to 25° C., and finally up to 190° C., in an argon atmosphere.

Polycrystalline $(C_4H_9NH_3)_2EuI_4$ samples were prepared using a low-temperature solid state reaction, with all synthetic steps and subsequent materials characterization being performed in an inert atmosphere. Stoichiometric amounts of europium(II) iodide (0.243 g, 0.6 mmole) and butylammonium iodide (0.241 g, 1.2 mmole) were weighed in an argon-filled drybox with oxygen and water levels maintained below 1 ppm. An intimate mixture of the two starting materials was pressed into pellets and subsequently placed into a quartz tube, which had been thoroughly dried by heating under vacuum before being brought into the drybox.

In addition to the stoichiometric pellets, a few flakes (approximately 0.010 g) of additional $C_4H_9NH_2 \cdot HI$ were also added to the reaction tube.

The conditions for the solid state reaction were chosen based on differential thermal analysis (DTA) and thermogravimetric analysis (TGA) performed on similarly prepared mixtures of unreacted starting materials as described below. The reaction tube, containing an argon atmosphere, was sealed and placed into a preheated 140° C. tube furnace. After maintaining the temperature at 140° C. for 5 days, the temperature was raised to 150° C. for 4 days, and to 160° C. for 8 hr, before finally being cooled over several hours. The initial weight of the pellets after pressing was 0.475(2) g, and after the heating cycle was 0.473(2) g, indicating that the overall composition of the pellets hadn't changed during the process. Infrared (IR) transmission spectroscopy, using KBr pellets containing the product, yielded the following major peaks ($cm^{-1}$): 903 m, 928 m, 1009 m, 1042 m, 1076 m, 1160 m, 1390 w, 1471 s, 1574 s, 2380 w, 2477 w, and a broad region of strong peaks, including 2874, 2931, 2962, 3050 (broad), 3168 (shoulder). The IR spectrum for the product was in good agreement with a spectrum taken for the starting material $C_4H_9NH_2 \cdot HI$, indicating that the organic cation remained intact after the heating cycle. By analogy with the lead(II) systems, it is expected that these compounds can also be deposited as thin films by spin casting and thermal evaporation.

Simultaneous thermogravimetric analysis (TGA) and differential thermal analysis (DTA) were performed, using a Seteram TAG 24 thermal analysis system, to examine the reactivity, thermal stability, and possible phase transitions in $(C_4H_9NH_3)_2EuI_4$. Measurements were made both on an unreacted, stoichiometric (2:1) mixture of $C_4H_9NH_2 \cdot HI$ and $EuI_2$, and on a sample of $(C_4H_9NH_3)_2EuI_4$ prepared as described above. In addition, the starting materials, $C_4H_9NH_2 \cdot HI$ and $EuI_2$, were also examined separately. Approximately 40–90 mg of sample was loaded into a tantalum container for each run. The thermal cycling was performed using a 2° C./min ramp rate in an argon atmosphere. Special care was taken to exclude oxygen from the apparatus by evacuating and back-filling the thermal analysis setup with argon. The temperature was calibrated using the melting transitions of indium ($T_m$=156° C.) and tin ($T_m$=231.9° C.) using the same system configuration (crucible type, temperature ramp rate, gas type, gas flow, etc.).

Room temperature X-ray powder diffraction patterns were collected for each batch of samples, using a Siemens D5000 diffractometer, and showed the products to be single phase. Since samples of $(C_4H_9NH_3)_2EuI_4$ degrade very rapidly in air, it was necessary to contain the sample in an air-tight cell during the diffraction run. Regions of each data set were collected twice to insure that the sample had not significantly degraded during the first scan.

All 30 of the observed peaks in the region $2° \leq 2\theta \leq 50°$ indexed to an orthorhombic unit cell with dimensions very similar to those observed for $(C_4H_9NH_3)_2MI_4$ (M=Ge, Sn, Pb). Of the 30 peaks, 28 were singly indexed (corresponded to one h,k,l), using an angular tolerance of 0.018°. The unit cell dimensions were refined using the Siemens WINMETRIC program (least squares approach), after stripping the Cu $K\alpha_2$ component from the diffraction pattern, yielding a=8.913(3) Å, b=8.759(3) Å, and c=27.793(6) Å.

For comparison, $(C_4H_9NH_3)_2PbI_4$ was also prepared using the same solid state technique as for the europium analog and examined using powder X-ray diffraction. Of the 48 peaks observed over the interval, $2° \leq 2\theta \leq 50°$, all indexed (with 44 singly indexed) to the orthorhombic unit cell, a=8.886(2) Å, b=8.698(2) Å, and c=27.637(5) Å.

For magnetic measurements, samples of $(C_4H_9NH_3)_2EuI_4$ were specially prepared by packing an intimate stoichiometric (2:1) mixture of $C_4H_9NH_2 \cdot HI$ and $EuI_2$ into a quartz cup before the heating cycle, rather than by pressing pellets in a die. This was done to avoid incorporating possible magnetic impurities from the metallic die. Besides this precaution, synthetic conditions were similar to those described above.

Magnetic measurements were performed in a Quantum Design SQUID magnetometer over the temperature range 1.8–300 K. For each magnetic measurement, approximately 80 mg of sample was used and the susceptibility was measured using an applied magnetic field of 50 Oe. The background of the sample holder was measured and subtracted from the sample measurement (it was several orders of magnitude weaker than the sample signal). The core diamagnetism for the atoms in the $(C_4H_9NH_3)_2EuI_4$ was also calculated and subtracted from the measured paramagnetism before determining the effective Eu magnetic moment.

Fluorescence emission spectra were recorded at room temperature on a Spex Fluorolog-2 Spectrometer using the front face geometry. Light from a xenon arc lamp was used as the excitation source after passing it through a SPEX 1680 0.22 m double spectrometer. The emitted fluorescence was also passed through a similar double spectrometer to a SPEX 1911F detector.

Spectra were recorded for solid samples of $(C_4H_9NH_3)_2EuI_4$ as well as for $EuI_2$ (as received from the manufacturer; Aldrich-APL, anhydrous, 99.9%). The solid samples were first ground into a fine powder and contained in an air-tight cell with a quartz window. Each spectrum was collected several times to ensure that the sample did not significantly degrade over the course of the measurement.

As a result of the organic component, which decomposes at relatively low temperatures (T>250° C.), organic-inorganic perovskites are typically made using relatively low-temperature solution chemistry techniques. Single crystals of many of the $A_2MX_4$ materials, with for example M=Cd, Cu, Fe, Mn, Pd, Ge, Sn, or Pb, can be grown by slow cooling or evaporating a solution containing the organic ammonium halide and the metal halide, with some of the more common solvents including, water, various alcohols, acetone, hydrohalic acids, and n-methyl-2-pyrrolidone. The solution chemistry of $Eu^{+2}$, however, is complicated by the fact that there is a strong tendency for solvent molecules to become tightly bound to the metal, thereby impeding the formation of the layered perovskites. In addition, $Eu^{+2}$ is susceptible to oxidation and is therefore not stable in many solvents, at least for the relatively long periods of time or the range of temperatures required to grow high quality crystals. Given the difficulties of solution chemistry, solid state techniques are potentially useful and have been used for the preparation of inorganic $Eu^{+2}$ ternary compounds. $AEuI_3$ (A=Cs, Rb) and $AEu_2I_5$ (A=K, Rb, Cs), for example, have been synthesized by the reaction of elemental Eu, AI (A=Cs, Rb), and $HgI_2$, in an evacuated sealed quartz tube. However, this reaction occurs at temperatures up to 560° C., conditions which would certainly lead to thermal decomposition of the organic cation in the case of the organic-inorganic perovskites.

Figure 2:
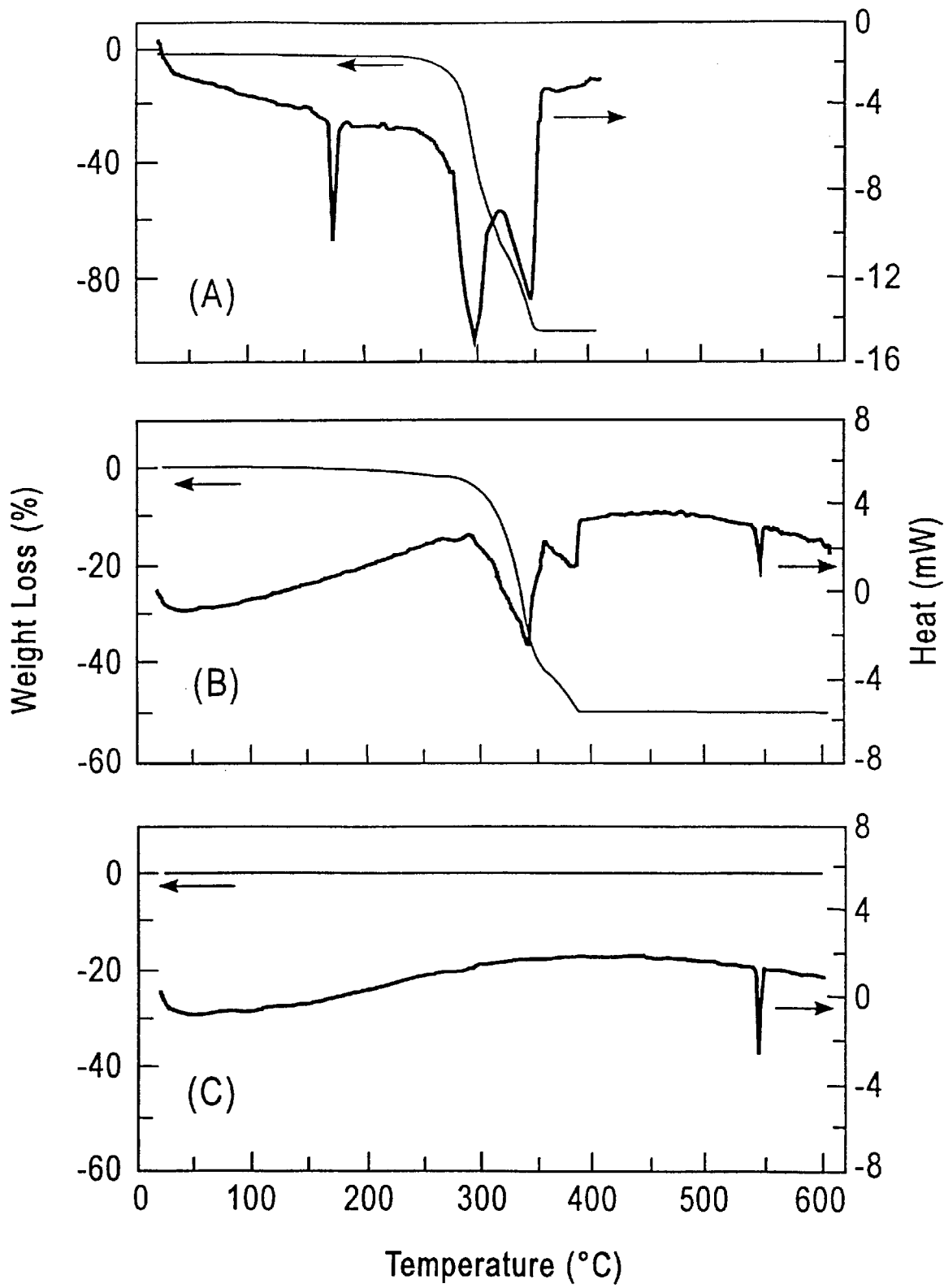
FIG. 2 shows the simultaneous thermogravimetric analysis (TGA) and differential thermal analysis (DTA) scans (heating portions) for (a) $C_4H_9NH_2 \cdot HI$, (b) $(C_4H_9NH_3)_2EuI_4$ prepared by solid state reaction and (c) $EuI_2$, each scan performed in flowing argon with a ramp rate of 2° C./min.

The direct solid state reactivity of the organic ammonium iodide with $EuI_2$, using simultaneous differential thermal analysis (DTA) and thermogravimetric analysis (TGA), was examined to determine whether a reaction would occur between the two components before the material decomposed. FIG. 1 shows the DTA/TGA curves for an intimate stoichiometric (2:1) mixture of $C_4H_9NH_2 \cdot HI$ and $EuI_2$. The temperature was ramped from room temperature to 175° C., back to approximately 25° C., and finally up to 190° C., all in an argon atmosphere. During the first heating segment, there is a weak exotherm that begins around 100° C. and finishes by 140° C. The exact temperature and width of this transition varied somewhat depending on how tightly the material was packed into the tantalum crucible, but in all cases it was completed by 160° C. There is essentially no weight loss associated with this transition and the exotherm is not present during the second pass through this temperature range. Consequently, the low temperature exotherm can be attributed to a reaction between the two starting materials. Further evidence of this can be deduced by a comparison with the thermal analysis curves for pure $C_4H_9NH_2 \cdot HI$ (FIG. 2B). The endotherm in this curve at 171(1)° C. corresponds to the melting of the organic ammonium salt, before its bulk decomposition at temperatures above 250° C. The absence of the endotherm in the DTA curve for the $C_4H_9NH_2 \cdot HI/EuI_2$ mixture during the second ramp up to 190° C. suggests that the $C_4H_9NH_2 \cdot HI$ has reacted with $EuI_2$.

FIG. 2B shows the thermal analysis curves for a section of a $(C_4H_9NH_3)_2EuI_4$ pellet, prepared at 160° C. as described in the experimental section. Again, there is no exotherm at low temperatures and no melting endotherm in the region 170°–200° C. There is also no sharp onset of weight loss as a function of temperature, but rather the material begins to slowly lose weight at temperatures as low as 150° C., with bulk decomposition occurring around 290° C. The weight loss during the decomposition corresponds to 50.3% of the initial weight. This is in good agreement with the expected weight loss (49.8%) for the complete loss of the organic component (in the form of $C_4H_9NH_2 \cdot HI$), leaving behind only the inorganic component of the compound, $EuI_2$. The endotherm at 543(1)° C. therefore apparently corresponds to the melting of $EuI_2$, an assertion which is supported by the DTA curve for pure $EuI_2$ (FIG. 2C), examined as received from the manufacturer (Aldrich-APL, anhydrous, 99.9%).

The thermal analysis curves for $(C_4H_9NH_3)_2EuI_4$ and the starting materials, $C_4H_9NH_2 \cdot HI$ and $EuI_2$, demonstrate several useful points about the synthesis and thermal stability of $(C_4H_9NH_3)_2EuI_4$. First, unlike $(C_4H_9NH_3)_2GeI_4$, for which it is possible to grow crystals from a stoichiometric melt, melt processing can not be used in this case (at least using a stoichiometric melt). Secondly, this invention demonstrates that solid state reactions can be used to react $C_4H_9NH_2 \cdot HI$ and $EuI_2$, without substantial decomposition. Since small weight losses are observed at relatively low temperatures in the TGA curves for $(C_4H_9NH_3)_2EuI_4$, the solid state reactions are carried out in a sealed tube containing an inert atmosphere, rather than in an open system where the organic component can continuously leave the system. In addition, a small excess of $C_4H_9NH_2 \cdot HI$ is included in the reaction tube, along with the stoichiometric $C_4H_9NH_2 \cdot HI/EuI_2$ pellets, to provide a partial pressure of $C_4H_9NH_2$ and HI in the ampoule and therefore discourage the loss of the organic cation from the pellets. The fact that there is essentially no weight change observed for the pellets before and after the heating cycle verifies that these conditions fulfill their purpose.

Figures 3A, 3B:
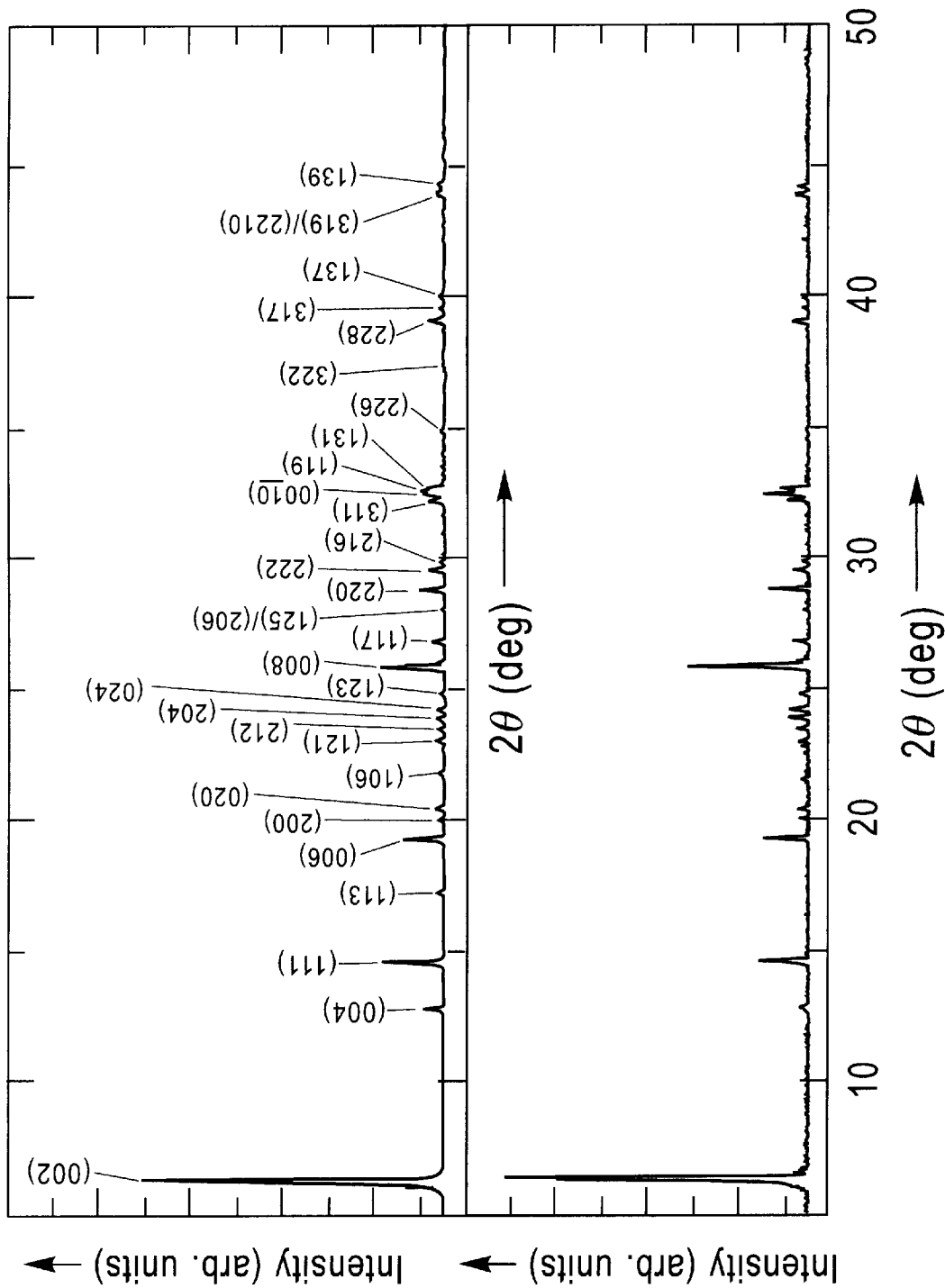
FIGS. 3A and 3B show room temperature X-ray powder diffraction patterns (Cu K$\alpha_1$ component) for (A) $(C_4H_9NH_3)_2EuI_4$, and (B) $(C_4H_9NH_3)_2PbI_4$ respectively.

FIG. 3A shows the powder X-ray pattern for $(C_4H_9NH_3)_2EuI_4$ prepared by solid state synthesis. The diffraction pattern is very similar to that observed for $(C_4H_9NH_3)_2PbI_4$ (FIG. 3B), prepared using a similar solid state reaction. For $(C_4H_9NH_3)_2EuI_4$, the refined orthorhombic lattice parameters are, a=8.913(3) Å, b=8.759(3) Å, c=27.793(6) Å, compared with a=8.886(2) Å, b=8.698(2) Å, c=27.637(5) Å for the Pb(II) analog. The very similar lattice constants, along with the virtually identical intensity ratios among the peaks of the diffraction patterns provide convincing evidence that the Eu(II) system adopts a layered perovskite structure analogous to that observed for the divalent Ge, Sn, and Pb halides. These structures all consist of layers of corner-sharing $MI_6$ octahedra separated by bilayers of the butylammonium cations. The ammonium heads of the organic cation hydrogen/ionic bond to the metal halide sheets and the hydrocarbon tails extend into the space between the layers.

The six-fold Eu(II) coordination in $(C_4H_9NH_3)_2EuI_4$ is similar to that observed in $CsEuI_3$, which adopts a three-dimensional distorted perovskite structure with the lattice constants, a=8.624(2) Å, b=17.968(5) Å, c=12.540(3) Å. This is in contrast to the situation for the room temperature (and ambient pressure) phase of $EuI_2$, where an unusual seven-fold coordination is observed. The a and b lattice parameters for $(C_4H_9NH_3)_2EuI_4$, which correspond to the values in the plane of the perovskite sheets, are approximately equal to $\sqrt{2}a_p$, where $a_p$ is the lattice parameter for an ideal cubic perovskite. The average value for this parameter, derived from the two in-plane lattice constants, is $a_p$=6.248 Å. By comparison, the orthorhombic lattice constants for $CsEuI_3$ approximately obey the relation $a=\sqrt{2}a_p$, $b=2\sqrt{2}a_p$, $c=2a_p$. The average value of $a_p$ derived using this relation is $a_p$=6.240 Å, a value very similar to that found in $(C_4H_9NH_3)_2EuI_4$. The $a_p$, derived using this approach does not necessarily yield exactly twice the Eu-I bond distance, as it would in a cubic perovskite, since the Eu-I-Eu bond angles between nearest-neighbor $EuI_6$ octahedra are not, in general, 180° (i.e. the octahedra can rotate to some degree relative to each other).

Magnetic measurements were undertaken for $(C_4H_9NH_3)_2EuI_4$ to examine the magnetic moment of europium in this material. Formally, europium should be present as $Eu^{2+}$, leading to a $^8S_{7/2}$ electronic ground state for the metal ion. Assuming that the europium ions are well isolated from each other (generally a very good assumption for rare earth ions), Curie's law should apply with an expected paramagnetic moment close to the free-ion value of $\mu_{eff}=g\mu_b(J(J+1))^{1/2}=7.94\mu_b$.

Figure 4:
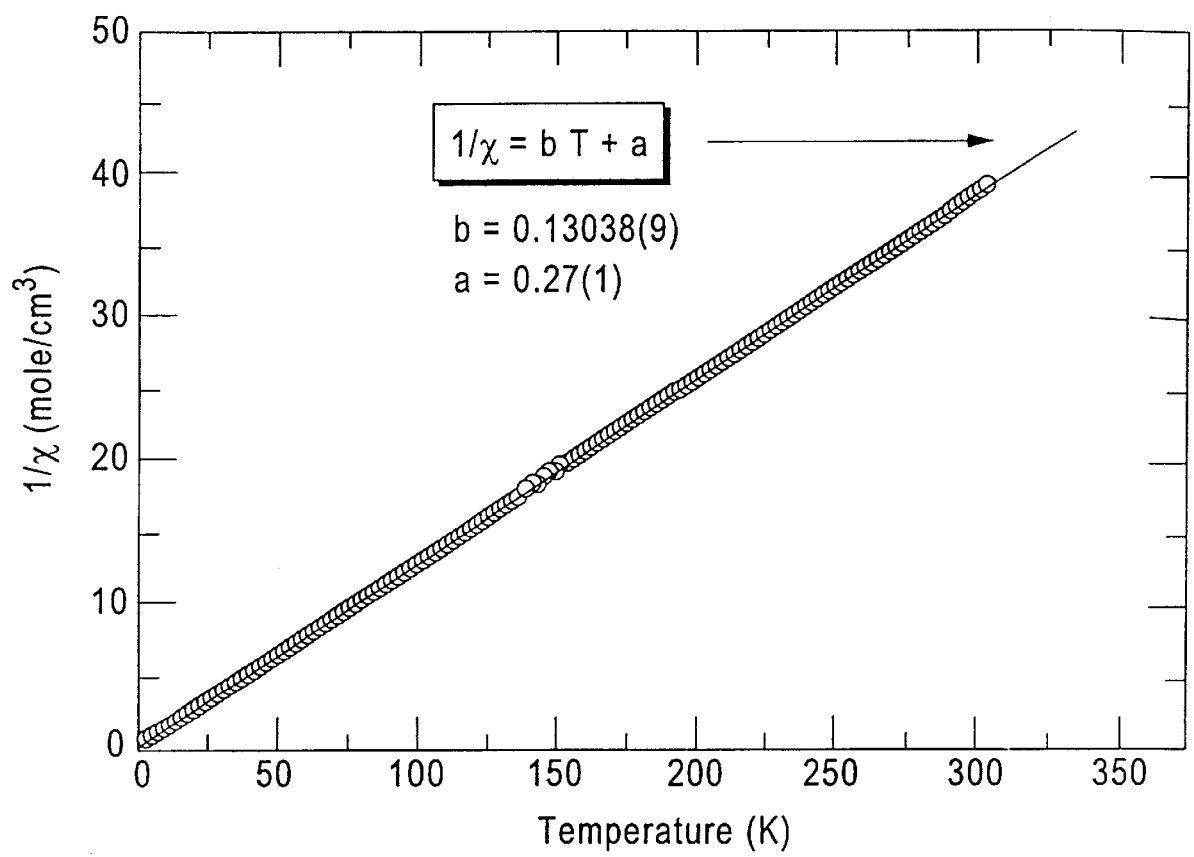
FIG. 4 shows the inverse magnetic susceptibility as a function of temperature for $(C_4H_9NH_3)_2EuI_4$ in an applied field of 50 Oe.

The inverse magnetic susceptibility of a sample of $(C_4H_9NH_3)_2EuI_4$ is shown as a function of temperature in FIG. 4, and is approximately a straight line. The slope of the line yields the derived paramagnetic moment for the europium ions, $7.8(1)\mu_b$, close to the predicted free-ion value and also very similar to the measured moments in $EuI_2$, $CsEuI_3$, and $RbEuI_3$. The Curie temperature, $\theta$, defined by $\chi=C/(T-\theta)$, is given by $\theta=-(a/b)$, where "a" and "b" are the coefficients of the straight line fit of the inverse susceptibility versus temperature data (FIG. 4). For the $(C_4H_9NH_3)_2EuI_4$ sample, we find $\theta=-2(1)$ K. The very small value for $\theta$, as well as the absence of magnetic ordering at temperatures above 1.8 K, demonstrates the small degree of interaction between the europium moments.

Figure 5:
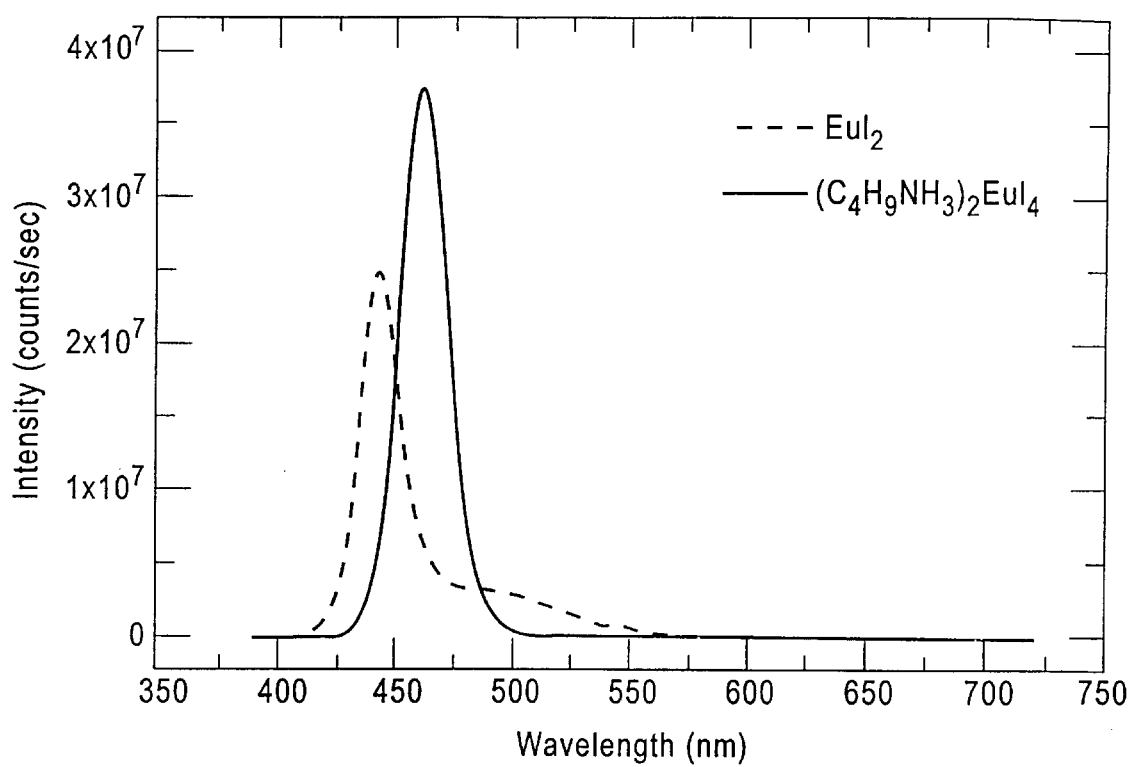
FIG. 5 shows the room temperature photoluminescence emission spectrum for ground solid state samples of $(C_4H_9NH_3)_2EuI_4$, and $EuI_2$ using an excitation wavelength of 370 nm for each spectrum.

FIG. 5 shows the fluorescence emission spectra of powders of $(C_4H_9NH_3)_2EuI_4$ and $EuI_2$. $EuI_2$ emits at 442(1) nm, along with a shoulder which extends out to approximately 500 nm, in good agreement with published results. $(C_4H_9NH_3)_2EuI_4$ powders give rise to a single, sharp, nearly symmetrical emission peak at 460(1) nm, a value which is red-shifted by approximately 18 nm relative to that for $EuI_2$.

The emission peak full-width at half maximum (or height), FWHM, is 24 nm, similar to that observed in the corresponding lead(II) iodide-based systems. The emission peak position appears to be relatively independent of excitation wavelength, although there is some variation in the intensity of the peak. The excitation spectrum (corresponding to the 460 nm emission) consists of several broad overlapping bands, ranging from a high energy band centered at 275 nm, to one which extends from approximately 330 nm to 425 nm. The lower energy band is very broad and clearly has several components.

As in $EuI_2$, the emission of $Eu^{2+}$ in $(C_4H_9NH_3)_2EuI_4$ is expected to result from the transition from the $4f^65d^1$ configuration to the ground state, $4f^7$. This assignment is based on the very similar spectral characteristics between the present compound and $EuI_2$, and especially with the detailed measurements made on $Eu^{2+}$ impurities in alkali halide hosts. The observed variability in the emission peak between $EuI_2$ and $(C_4H_9NH_3)_2EuI_4$ is further evidence that the luminescence observed in these systems arises from a radiative transition involving the $4f^65d$ configuration. In contrast to transitions within the 4f manifold, which should be fairly independent of the local coordination, transitions involving the more extended 5d orbitals should result in more sensitivity to crystal field effects. In the $Eu^{2+}$ doped alkali iodides, for example, the emission peak shifts to the blue as the lattice parameter is increased by inserting larger alkali atoms. The emission spectrum of $EuI_2$ has also been shown to depend on the structural details of the various high pressure and ambient pressure phases of this compound. Similarly, the red-shift between $EuI_2$ and $(C_4H_9NH_3)_2EuI_4$ most likely arises from the differences in local coordination. While $Eu^{2+}$ sits at the center of an octahedra within $(C_4H_9NH_3)_2EuI_4$, it adopts an unusual seven-fold coordination within $EuI_2$. It is surmised that the average Eu-I distance in the seven-fold coordinated compound should be longer than in the six-fold coordinated compound.

In the lead(II)-based (as well as the tin(II)- and germanium(II)-based) organic-inorganic perovskites, luminescence arises from the radiative decay of free excitons associated with the two-dimensional inorganic sheets in the structure. In the purely inorganic $PbI_2$, the luminescence from the excitons is quenched at room temperature as a result of the small exciton binding energy (approximately 30 meV). In contrast, the exciton binding energies in the lead(II)-based organic-inorganic perovskites is on the order of 200–400 meV, enabling the strong photoluminescence associated with these excitons to be observed even at room temperature. The enhancement in binding energy is the result of the two-dimensionality of the structure, combined with an enhancement in the electron-hole coulomb interaction arising from the smaller dielectric constant for the organic layers which sandwich the metal halide sheets.

In addition to the unusually strong binding energy, the effective dimensionality of the lead(II) halide sheets has a substantial impact on the wavelength at which luminescence is observed through a "quantum confinement effect". Specifically, as the thickness of the perovskite sheets increases (i.e. for example, by increasing "n" in the family $(C_{10}H_{21}NH_3)_2(CH_3NH_3)_{n-1}Pb_nI_{3n+1})$ the luminescence peak shifts to substantially longer wavelength, ranging from 524 nm for n=1 to 753 nm for the three-dimensional n=∞ compound (i.e. $CH_3NH_3PbI_3$). This fairly dramatic shift in the luminescence spectrum can readily be understood by a bandgap reduction with increasing perovskite sheet thickness, and is the same effect that leads to a semiconductor-metal transition as a function of increasing perovskite sheet thickness in the family $(C_4H_9NH_3)_2(CH_3NH_3)_{n-1}Sn_nI_{3n+1}$.

In contrast to the lead(II) and tin(II) organic-inorganic perovskite families, the luminescence in the europium(II) compounds is less sensitive to global structural details. For the layered compound, $(C_4H_9NH_3)_2EuI_4$ (i.e. n=1), the luminescence peak is at 460 nm. For the three-dimensional system, $CsEuI_3$, the emission peak is at 449 nm, while for $CH_3NH_3EuI_3$ (which has recently been found to adopt a similar tetragonally distorted perovskite structure as that observed at room temperature in $CH_3NH_3PbI_3$), the peak is at 448(1) nm. Consequently, the emission spectrum peak wavelength for the europium(II) systems occurs at very similar wavelengths for the three-dimensional perovskites and the two-dimensional layered system. In fact, the emission peak shifts in the opposite direction to what one would expect for the "dimensional confinement effect". This is presumably because of the different nature of the excitation giving rise to the luminescence in the two systems. Whereas in the lead(II), tin(II), and germanium(II) systems, the luminescence arises from the radiative decay of free excitons associated with the material's band gap, the luminescence in the europium(II) system appears to arise from a more local excitation centered on the europium(II) ion, which is therefore less sensitive to the overall dimensionality of the structure.

The photoluminescence in $(C_4H_9NH_3)_2EuI_4$ is surprisingly found to be more robust than in $(C_4H_9NH_3)_2PbI_4$. For the lead(II) compound, strong green luminescence is observed at room temperature in well-crystallized single crystals, but virtually no luminescence is observed in poorly crystallized samples, in finely ground crystals, or in pressed pellets of the material prepared by solid state synthesis. In contrast, the europium(II) samples luminesce very strongly even in fine powders made using the solid state technique. Presumably, this is also because the electronic states responsible for the luminescence are more localized in the europium compound. In the lead(II) systems, the excitons are more free to diffuse to defects, which can act as non-radiative decay centers.

In all other analogous families of $A_2MX_4$ compounds, with M=a divalent transition metal cation or a Group 14 metal cation (e.g., Ge, Sn, or Pb), a wide range of organic cations can occupy the "A" site in the structure, including those based on aliphatic amines, simple aromatic amines and more complex organic cations. It is therefore expected that in addition to the simple aliphatic ammonium cations of the form $C_nH_{2n+1}NH_3^+$, e.g., propylammonium ($C3H_7NH_3$) and butylammonium ($C_4H_9NH_3$), a wide range of simple aromatic organic cations, such as phenethylammonium ($C_6H_5C_2H_4NH_3^+$), and more functional organic cations including those that incorporate dye molecules, such as stilbene, oligothiophene and terphenyl derivatives, may also be substituted into the "A" sites of the current family of novel organic-inorganic $A_2MX_4$ perovskites. In the case of the $AMX_3$ compounds, the substitution of other organic cations for methylammonium should also be possible, but to a more limited extent due to the geometric and chemical constraints posed by the AMX3 structure.

Finally, the structural similarity between $(C_4H_9NH_3)_2EuI_4$ and the families $(C_4H_9NH_3)_2MI_4$, where M=Ge, Sn, Pb, suggests that mixed-metal solid solutions, $(C_4H_9NH_3)_2M_{1-y}M'_yX_4$, where M=a divalent rare earth metal, M'=a divalent metal (e.g., Ge, Sn, Pb) including a divalent rare earth metal or an alkaline earth (e.g., Ca, Sr) and X=a halogen (e.g., Cl, Br, I) may also be achievable using a similar procedure to that described for making the pure europium and lead compounds. In addition, given the similar chemical behavior of the rare earth metals, it is expected that other rare earth metals can be substituted for Eu in $(C_4H_9NH_3)_2EuI_4$ as well as in the $AMX_3$ compounds.

Figure 6:
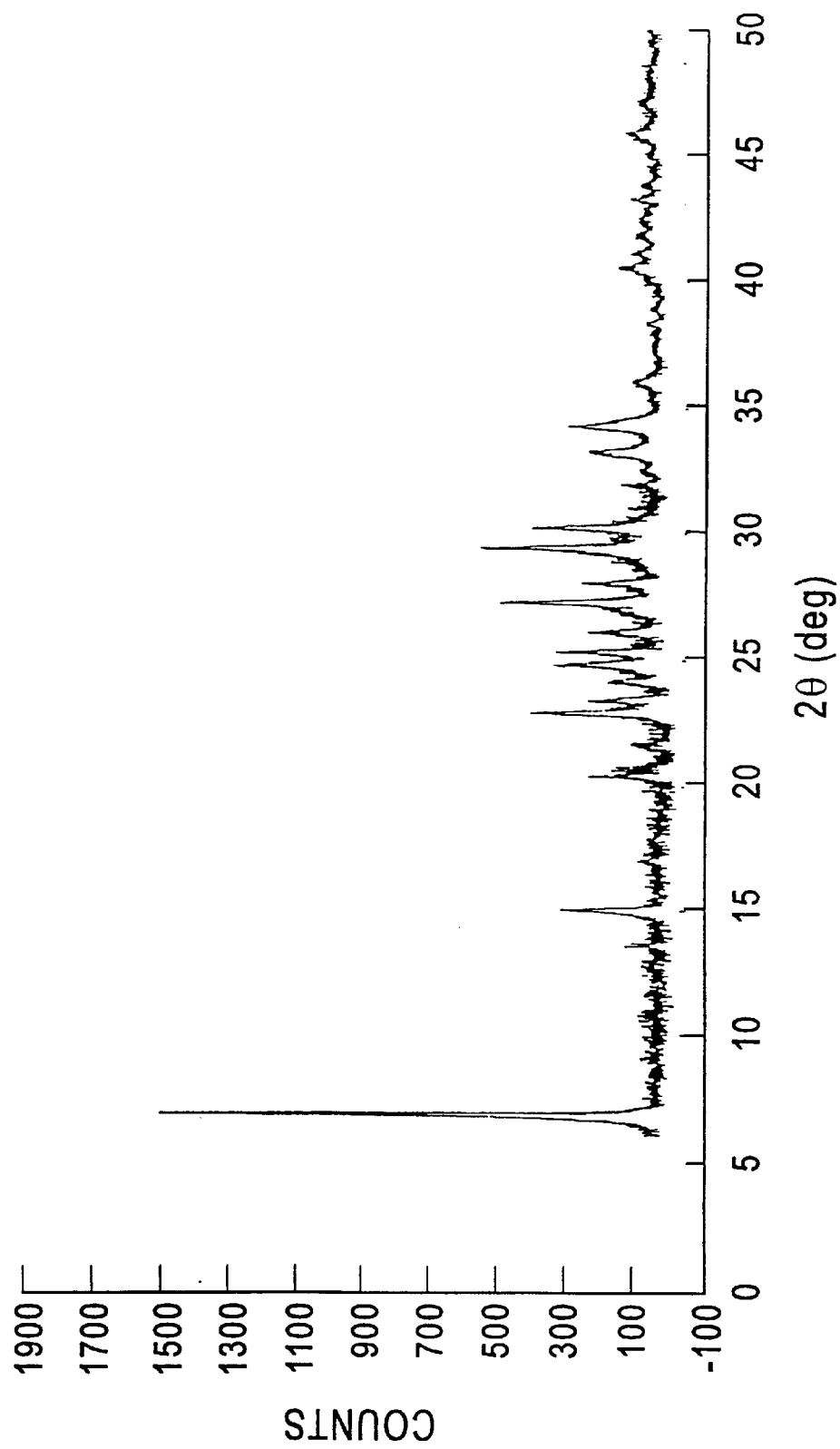
FIG. 6 shows the room temperature X-ray powder diffraction pattern (Cu K$\alpha_1$ component) for $(C_3H_7NH_3)_2YbI_4$.

These possibilities are illustrated by FIG. 6 which shows the diffraction pattern for the new compound propylammonium ytterbium(II) iodide, $(C_3H_7NH_3)_2YbI_4$, which was made using a similar solid state procedure described above for making $(C_4H_9NH_3)_2EuI_4$. This Figure shows that the compound forms a similar layered perovskite structure as that observed for $(C_4H_9NH_3)_2EuI_4$.

What is claimed is:

1. A compound of the general formula $A_2MX_4$, where A is an organic ammonium cation, M is a divalent rare earth metal cation and X is a halogen, and having a layered organic-inorganic perovskite structure.

2. A compound as in claim 1 wherein A is an organic ammonium cation selected from the group consisting of aliphatic ammonium cations, simple aromatic ammonium cations and functional organic ammonium cations.

3. A compound as in claim 1 wherein A is butylammonium, M is europium and X is iodine.

4. A compound as in claim 1 wherein A is propylammonium, M is ytterbium and X is iodine.

5. A compound of the general formula $AMX_3$, where A is an organic ammonium cation, M is a divalent rare earth metal cation and X is a halogen, and having a perovskite structure.

6. A compound as in claim 5 wherein A is methylammonium, M is europium and X is iodine.

* * * * *